United States Patent
Fukuda et al.

(10) Patent No.: US 10,278,660 B2
(45) Date of Patent: May 7, 2019

(54) MEDICAL IMAGING APPARATUS AND METHOD FOR DISPLAYING A SELECTED REGION OF INTEREST

(71) Applicant: FUJIFILM Corporation, Tokyo (JP)

(72) Inventors: Wataru Fukuda, Ashigarakami-gun (JP); Junya Morita, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 597 days.

(21) Appl. No.: 14/970,620

(22) Filed: Dec. 16, 2015

(65) Prior Publication Data

US 2016/0095563 A1    Apr. 7, 2016

Related U.S. Application Data

(63) Continuation of application No. PCT/JP2014/003280, filed on Jun. 18, 2014.

(30) Foreign Application Priority Data

Jun. 21, 2013 (JP) ................................. 2013-130533

(51) Int. Cl.
*G06T 7/55* (2017.01)
*A61B 6/00* (2006.01)
(Continued)

(52) U.S. Cl.
CPC .............. *A61B 6/465* (2013.01); *A61B 6/461* (2013.01); *A61B 6/463* (2013.01); *G06T 7/50* (2017.01);
(Continued)

(58) Field of Classification Search
CPC ... A61N 1/00; A61N 1/02; A61N 1/04; A61N 1/0472; A61N 1/0476; A61N 1/08;
(Continued)

(56) References Cited

U.S. PATENT DOCUMENTS

| | | |
|---|---|---|
| 5,940,527 A | 8/1999 | Takeo |
| 8,983,156 B2 | 3/2015 | Periaswamy et al. |

(Continued)

FOREIGN PATENT DOCUMENTS

| | | |
|---|---|---|
| JP | 6-14915 A | 1/1994 |
| JP | 8-294479 A | 11/1996 |

(Continued)

OTHER PUBLICATIONS

Communication dated Dec. 13, 2016, from the Japanese Patent Office in counterpart Japanese application No. 2015-522561.

(Continued)

*Primary Examiner* — Anastasia Midkiff
(74) *Attorney, Agent, or Firm* — Sughrue Mion, PLLC

(57) ABSTRACT

When at least one of a two-dimensional radiological image and a plurality of tomographic images of the same subject is displayed on a monitor, a depth map creation unit creates a depth map in which each position on the pseudo two-dimensional image is associated with depth information indicating the position of a tomographic plane corresponding to each position in a depth direction. A display control unit specifies the depth information of a predetermined position in the two-dimensional radiological image, with reference to the depth map, and displays the tomographic image of the tomographic plane indicated by the specified depth information on the monitor.

18 Claims, 10 Drawing Sheets

(51) Int. Cl.
*A61B 6/02* (2006.01)
*A61B 6/04* (2006.01)
*G06T 7/00* (2017.01)
*G06T 7/50* (2017.01)
*A61B 34/00* (2016.01)
*A61B 34/20* (2016.01)
*G06T 11/00* (2006.01)

(52) U.S. Cl.
CPC .................. *G06T 7/55* (2017.01); *G06T 7/97* (2017.01); *G06T 11/003* (2013.01); *A61B 6/025* (2013.01); *A61B 6/0414* (2013.01); *A61B 6/464* (2013.01); *A61B 6/502* (2013.01); *A61B 6/5294* (2013.01); *A61B 34/25* (2016.02); *A61B 2034/2068* (2016.02); *G01N 2223/419* (2013.01)

(58) Field of Classification Search
CPC ...... A61N 5/00; A61N 5/0626; A61N 5/0627; A61N 5/10; A61N 5/103; A61N 5/1031; A61N 5/1039; A61N 5/1048; A61N 5/1049; A61N 5/1064; A61N 5/1071; A61N 5/1075; A61N 2005/1041; A61N 2005/1061; A61N 2005/1062; A61N 2005/1072; A61B 6/00; A61B 6/04; A61B 6/0407; A61B 6/0414; A61B 6/42; A61B 6/4208; A61B 6/4233; A61B 6/46; A61B 6/461; A61B 6/463–6/465; A61B 6/467; A61B 6/469; A61B 6/48; A61B 6/486; A61B 6/50; A61B 6/502; A61B 6/52; A61B 6/5211; A61B 6/5217; A61B 6/5223; A61B 6/5229; A61B 6/5235; A61B 6/5294; A61B 34/00; A61B 34/10; A61B 34/20; A61B 34/25; A61B 2576/00; A61B 2576/02; A61B 2560/00; A61B 2560/02; A61B 2560/0266; A61B 2034/101; A61B 2034/107; A61B 2034/2046; A61B 2034/2065; A61B 2034/2068; A61B 2034/2074; G06T 1/00; G06T 1/0007; G06T 3/00; G06T 3/0031; G06T 3/0037; G06T 3/40; G06T 3/4038; G06T 11/00; G06T 11/003; G06T 11/006; G06T 11/008; G06T 2200/00; G06T 2200/04; G06T 2200/28; G06T 2200/32; G06T 2211/00; G06T 2211/40; G06T 7/00; G06T 7/0002; G06T 7/0012; G06T 7/0014; G06T 7/0016; G06T 7/30; G06T 7/32; G06T 7/33; G06T 7/337; G06T 7/344; G06T 7/37; G06T 7/38; G06T 7/50; G06T 7/55; G06T 7/586; G06T 7/70; G06T 7/73–7/75; G06T 7/97; G06T 2207/00; G06T 2207/10; G06T 2207/10072; G06T 2207/10076; G06T 2207/10081; G06T 2207/10116; G06T 2207/10124; G06T 2207/20; G06T 2207/20092; G06T 2207/20101; G06T 2207/20104; G06T 2207/20108; G06T 2207/30; G06T 2207/30004; G06T 2207/30068; G06T 2210/00; G06T 2210/36; G06T 2210/41; G06T 2219/00; G06T 2219/008; G01N 2223/00; G01N 2223/40; G01N 2223/401; G01N 2223/402; G01N 2223/419; G01N 2223/425

See application file for complete search history.

(56) References Cited

U.S. PATENT DOCUMENTS

| | | | |
|---|---|---|---|
| 2003/0194050 | A1 | 10/2003 | Eberhard et al. |
| 2005/0111616 | A1 | 5/2005 | Li et al. |
| 2007/0013710 | A1* | 1/2007 | Higgins ............. A61B 1/00147 345/581 |
| 2008/0025459 | A1 | 1/2008 | Shi et al. |
| 2009/0080765 | A1* | 3/2009 | Bernard ............... G06T 11/006 382/154 |
| 2010/0074493 | A1 | 3/2010 | Wiemker et al. |
| 2012/0069957 | A1 | 3/2012 | Nakayama |
| 2012/0300899 | A1 | 11/2012 | Tajima |

FOREIGN PATENT DOCUMENTS

| | | |
|---|---|---|
| JP | 10-97624 A | 4/1998 |
| JP | 2003-325499 A | 11/2003 |
| JP | 2005-152658 A | 6/2005 |
| JP | 2005304831 A | 11/2005 |
| JP | 2008-29844 A | 2/2008 |
| JP | 2008-93254 A | 4/2008 |
| JP | 2010510859 A | 4/2010 |
| JP | 2011-139788 A | 7/2011 |
| JP | 2012-47671 A | 3/2012 |
| JP | 2012061187 A | 3/2012 |
| JP | 2012-245060 A | 12/2012 |
| WO | 2015046465 A1 | 4/2015 |

OTHER PUBLICATIONS

International Search Report for PCT/JP2014/003280 dated Oct. 7, 2014.
Written Opinion for PCT/JP2014/003280 dated Oct. 7, 2015.

* cited by examiner

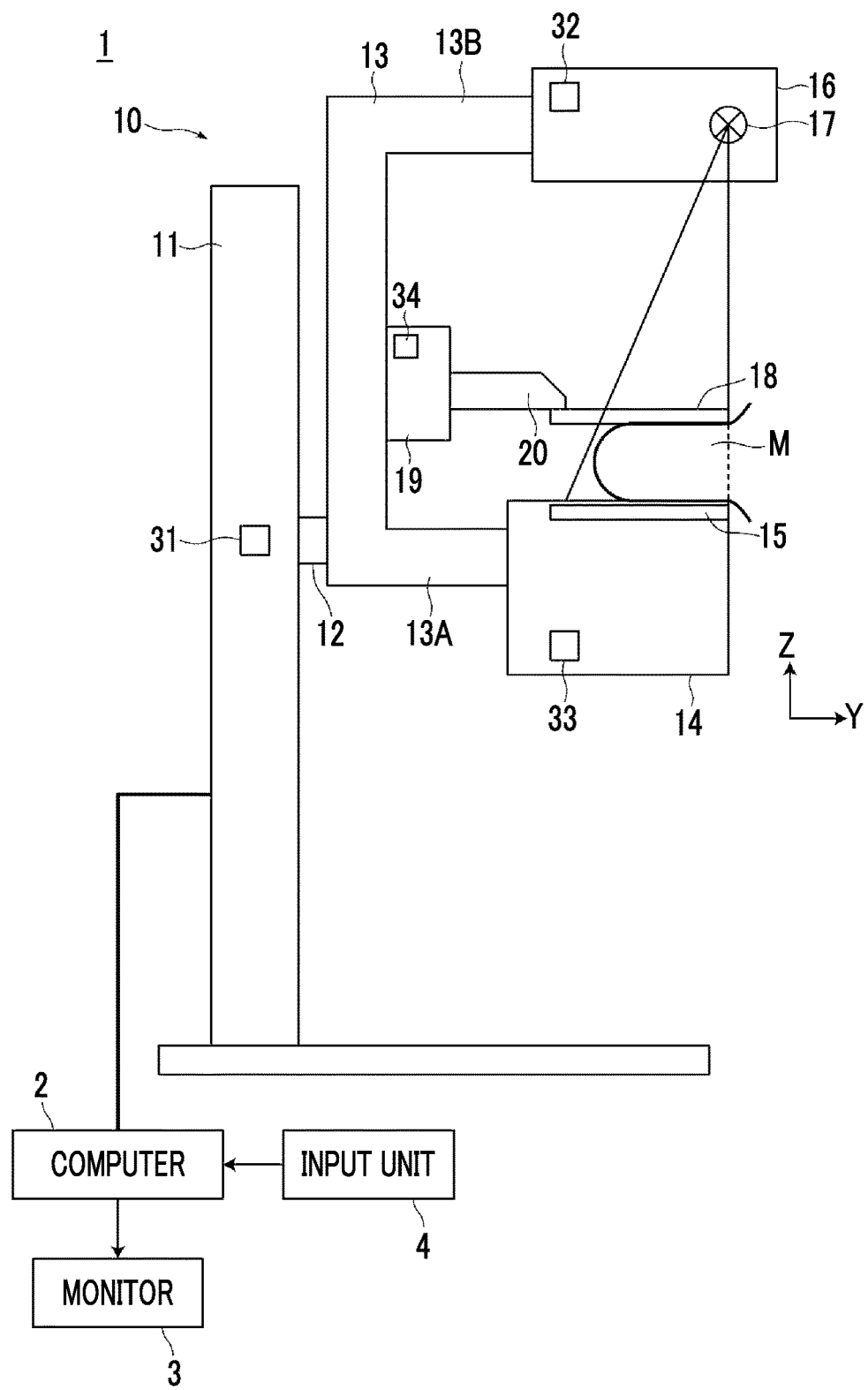

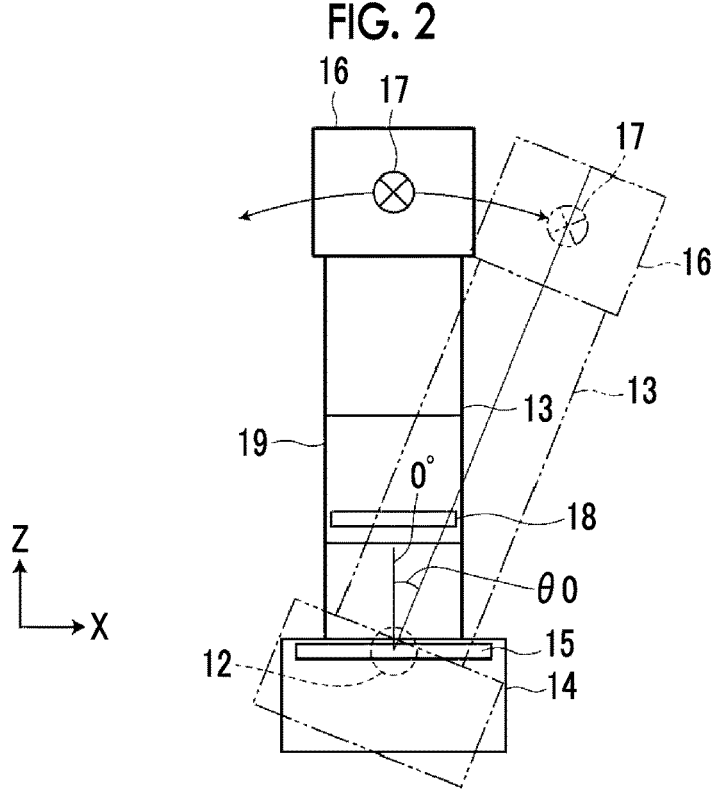
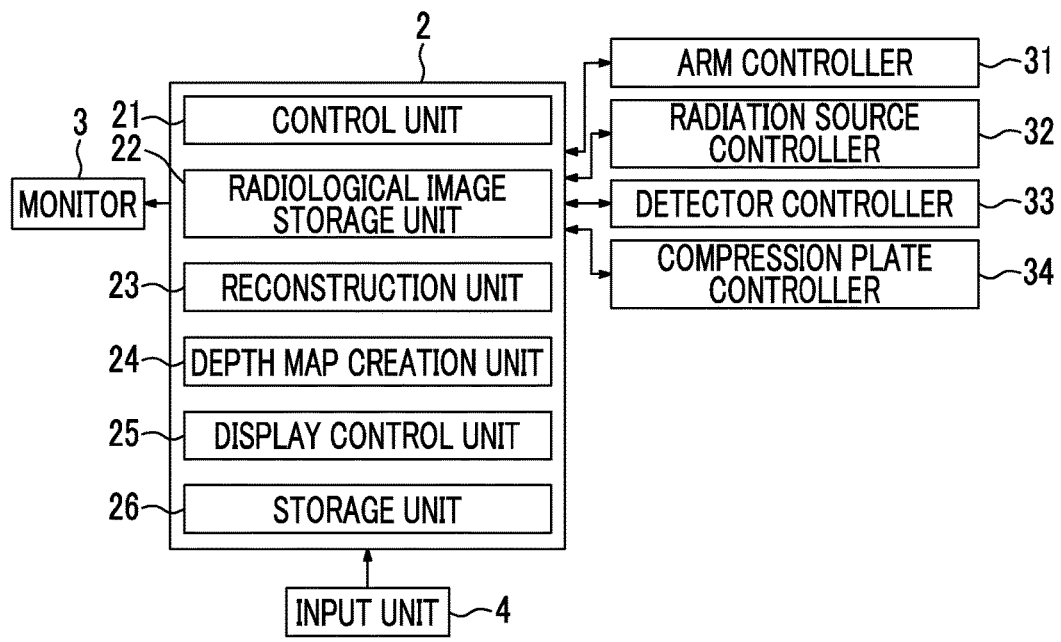

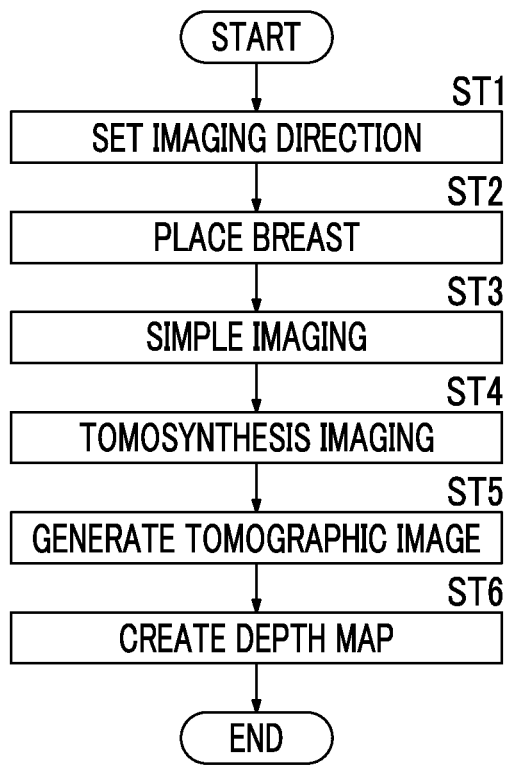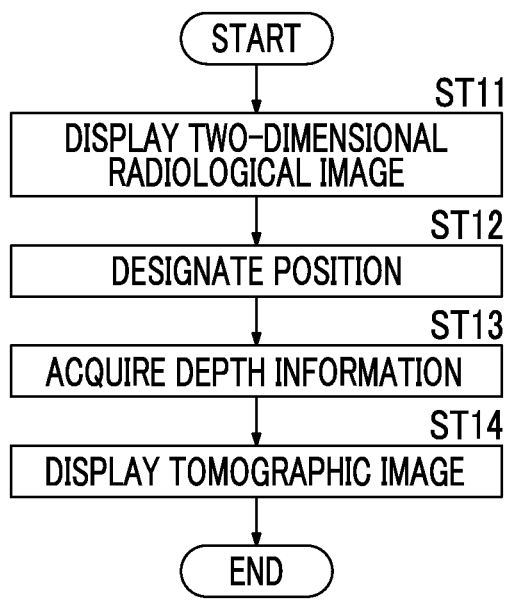

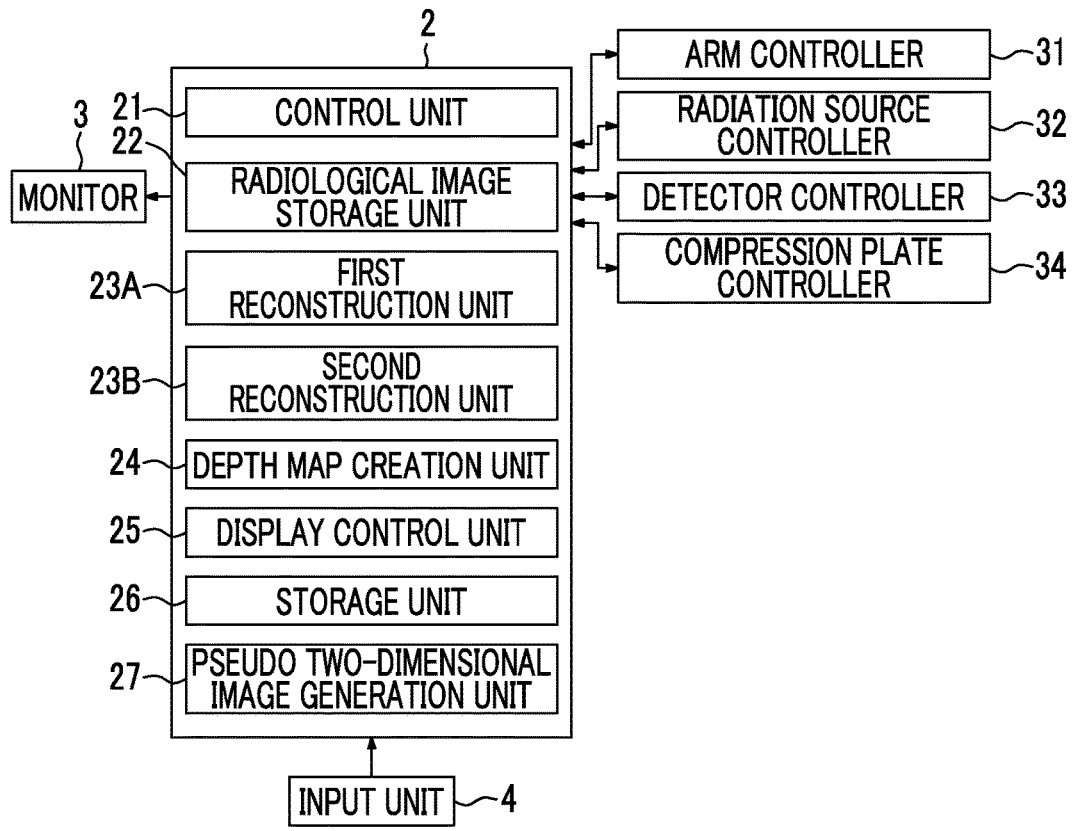
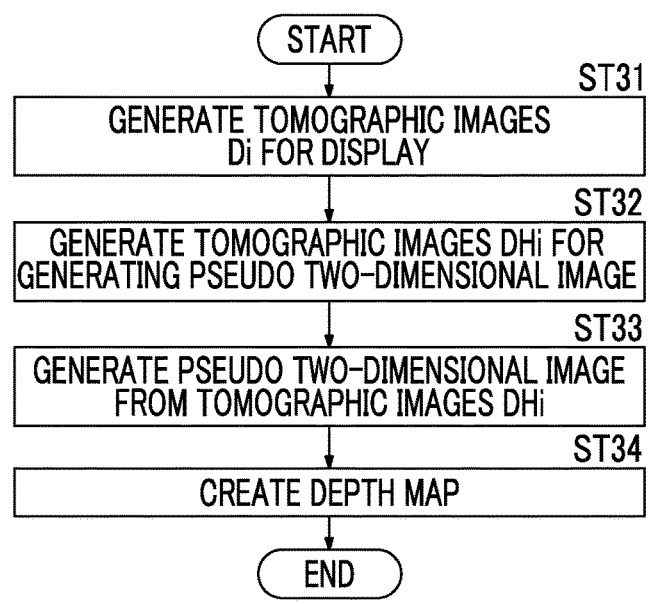

MEDICAL IMAGING APPARATUS AND METHOD FOR DISPLAYING A SELECTED REGION OF INTEREST

CROSS-REFERENCE TO RELATED APPLICATIONS

This application is a Continuation of PCT International Application No. PCT/JP2014/003280 filed on Jun. 18, 2014, which claims priority under 35 U.S.C. § 119 (a) to Japanese Patent Application No. 2013-130533 filed on Jun. 21, 2013. Each of the above applications is hereby expressly incorporated by reference, in its entirety, into the present application.

BACKGROUND OF THE INVENTION

1. Field of the Invention

The present invention relates to an image display device and method which displays a two-dimensional radiological image acquired by simple imaging and a tomographic image acquired by tomography, such as tomosynthesis imaging, and a program that causes a computer to perform an image display method.

2. Description of the Related Art

A medical image, such as a radiological image, is displayed and image diagnosis is performed with reference to a two-dimensional radiological image acquired by simple imaging and a tomographic image acquired by tomography using, for example, a CT device, an MRI device, or a tomosynthesis imaging device. For example, in order to perform diagnostic breast imaging, it is checked whether there is a lesion (tumor or calcification) in the breast, with reference to a two-dimensional radiological image which is acquired by simple imaging in various imaging directions, such as cranio-caudal (CC) imaging which emits radiation from the top to capture an image, medial-lateral (ML) imaging which emits radiation from the side to capture an image, and mediolateral-oblique (MLO) imaging which emits radiation in an oblique direction to capture an image, and a tomographic image which is generated by reconstructing a plurality of radiological images acquired by tomosynthesis imaging in each imaging direction.

Tomosynthesis imaging is an imaging method which irradiates the subject in a plurality of different directions to capture images while moving a radiation source and reconstructs the acquired image to obtain an image in which a desired tomographic plane is emphasized. In tomosynthesis imaging, the radiation source is moved parallel to the radiation detector or is moved in a circle or an arc of an ellipse, according to the characteristics of an imaging device or a necessary tomographic image, and the images of the subject are captured at a plurality of irradiation positions with different irradiation angles to acquire a plurality of radiological images. Then, the radiological images are reconstructed by a back projection method, such as a simple back projection method or a filtered back projection method, to generate a tomographic image.

The two-dimensional radiological image has the advantages of high consistency, high sharpness, and ease of comparison with the previous images over the tomographic image. Therefore, cross-referencing between the two-dimensional radiological image and the tomographic image is performed as follows. First, the two-dimensional radiological image is displayed on a display device, such as a liquid crystal monitor, and image diagnosis is performed. A position which is considered as a lesion on the two-dimensional radiological image is clicked and designated. Then, the tomographic image in which an area in the vicinity of the lesion is enlarged is displayed. In addition, in some cases, the two-dimensional radiological image and the tomographic image corresponding to the imaging direction of the two-dimensional radiological image are simultaneously displayed on the display device for cross-referencing. In any case, the tomographic image is displayed while the tomographic planes are automatically or manually switched.

A plurality of tomographic images are acquired by tomography such as tomosynthesis imaging. However, since the tomographic images include the tomographic image of the tomographic plane including, for example, the lesion and a tomographic image of a tomographic plane without including the lesion, the user, such as the doctor who performs image diagnosis, needs to read a plurality of tomographic images while switching the tomographic images. Therefore, when image diagnosis is performed with reference to both the two-dimensional radiological image and the tomographic image, the operation is more complicated than when only the two-dimensional radiological image is used. As a result, it takes a long time to perform diagnosis.

In order to solve the problems, a method has been proposed which receives a designated area of interest, such as a lesion, on a displayed two-dimensional radiological image, compares the image of the area of interest with the image of a corresponding area corresponding to the area of interest using image analysis, detects a tomographic image in which the image of the corresponding area is similar to the image of the area of interest on the basis of the analysis result, detects a tomographic image in which the image of a corresponding position is similar to the image of the area of interest when the area of interest is designated in the two-dimensional radiological image, and displays the tomographic image (see JP2012-245060A).

In addition, a method has been proposed which generates a maximum intensity projection (MIP) image or a minimum intensity projection (MinIP) image (hereinafter, referred to as an MIP image) from a tomographic image acquired by CT, using a projection method, such as an MIP method or an MinIP method, creates a depth information table in which depth information indicating the position of a pixel, which has the brightness value of the MIP image, in a basic tomographic image in the depth direction is stored for each MIP image, specifies the depth information of a designated position with reference to the depth table when an arbitrary position on the MIP image is designated, and displays the tomographic image of the tomographic plane at the depth indicated by the depth information (see JP2011-139788A).

SUMMARY OF THE INVENTION

However, in the method disclosed in JP2012-245060A, after the designated area of interest is received, image analysis is performed. Therefore, it takes a long time to perform an operation of detecting and displaying the tomographic image and it is difficult to perform a process in real time. The method disclosed in JP2011-139788A can display the tomographic image in a relatively short time since it refers to the depth information table. However, since the MIP image is displayed in order to receive the designated position, the two-dimensional radiological image acquired by simple imaging and the tomographic image are not mutually referred to.

The invention has been made in view of the above-mentioned problems and an object of the invention is to provide a technique which can rapidly display a tomographic image corresponding to a designated position when image diagnosis is performed with reference to both a two-dimensional radiological image and a tomographic image.

According to an aspect of the invention, there is provided an image display device including: display means for displaying at least one of a two-dimensional radiological image and a plurality of tomographic images of the same subject; and depth map creation means for creating a depth map in which each position on the two-dimensional radiological image is associated with depth information indicating a position of a tomographic plane corresponding to each position in a depth direction.

In the image display device according to the above-mentioned aspect of the invention, the depth map creation means may create the depth map on the basis of a positional relationship between a position of a radiation source when the two-dimensional radiological image is captured and a position of detection means for acquiring the two-dimensional radiological image.

The image display device according to the above-mentioned aspect of the invention may further include pseudo two-dimensional image generation means for generating a pseudo two-dimensional image from the plurality of tomographic images. The depth map creation means may create a temporary depth map in which each position on the pseudo two-dimensional image is associated with depth information indicating a position of a tomographic plane corresponding to each position in the depth direction and may create the depth map, on the basis of the temporary depth map and a correspondence relationship between each position on the two-dimensional radiological image and each position on the pseudo two-dimensional image.

For example, an MIP image which is generated by the maximum intensity projection method can be used as the pseudo two-dimensional image.

In the image display device according to the above-mentioned aspect of the invention, the depth map creation means may deform the temporary depth map, on the basis of the correspondence relationship between each position on the two-dimensional radiological image and each position on the pseudo two-dimensional image, to create the depth map.

The image display device according to the above-mentioned aspect of the invention may further include pseudo two-dimensional image generation means for generating a pseudo two-dimensional image from the plurality of tomographic images. The depth map creation means may associate each position on the pseudo two-dimensional image with depth information indicating a position of a tomographic plane corresponding to each position in the depth direction, to create the depth map.

The image display device according to the above-mentioned aspect of the invention may further include two-dimensional image generation means for generating a pseudo two-dimensional image as the two-dimensional radiological image from a tomographic image which is different from the plurality of tomographic images and is acquired by a reconstruction process. The depth map creation means may create a depth map in which each position on the generated two-dimensional radiological image is associated with depth information indicating a position of a tomographic plane corresponding to each position in the depth direction.

In the image display device according to the above-mentioned aspect of the invention, the depth map creation means may associate each position on the two-dimensional radiological image with the depth information indicating the position of the tomographic plane corresponding to each position in the depth direction, on the basis of a correlation between each position on the two-dimensional radiological image and the plurality of tomographic images, to create the depth map.

In the image display device according to the above-mentioned aspect of the invention, the depth map creation means may divide the two-dimensional radiological image into a plurality of areas and associate a position of each area on the two-dimensional radiological image with depth information indicating a position of a tomographic plane corresponding to the position of each area in the depth direction, to create the depth map.

The image display device according to the above-mentioned aspect of the invention may further include display control means for specifying depth information of a predetermined position on the two-dimensional radiological image, with reference to the depth map, and displaying a tomographic image of a tomographic plane indicated by the specified depth information on the display means.

The image display device according to the above-mentioned aspect of the invention may further include input means for receiving an arbitrary position which is designated on the two-dimensional radiological image displayed on the display means. The display control means may display the tomographic image on the display means, using the designated position as the predetermined position.

The image display device according to the above-mentioned aspect of the invention may further include abnormal shadow detection means for detecting an abnormal shadow included in the two-dimensional radiological image. The display control means may display the tomographic image on the display means, using a position of the detected abnormal shadow as the predetermined position.

In the image display device according to the above-mentioned aspect of the invention, the display means may display the tomographic image in the vicinity of the two-dimensional radiological image.

In the image display device according to the above-mentioned aspect of the invention, the display means may display the tomographic image so as to be superimposed on the two-dimensional radiological image.

According to another aspect of the invention, there is provided a radiological image capture and display system including: imaging means for acquiring a two-dimensional radiological image and a plurality of tomographic images of the same subject; and the image display device according to the above-mentioned aspect of the invention.

According to still another aspect of the invention, there is provided an image display method including: displaying at least one of a two-dimensional radiological image and a plurality of tomographic images of the same subject; and creating a depth map in which each position on the two-dimensional radiological image is associated with depth information indicating a position of a tomographic plane corresponding to each position in a depth direction.

According to yet another aspect of the invention, there is provided an image display device including: pseudo two-dimensional image generation means for generating a pseudo two-dimensional image from a plurality of tomographic images of the same subject; display means for displaying at least one of the pseudo two-dimensional image and the plurality of tomographic images; and depth map creation means for creating a depth map in which each position on the pseudo two-dimensional image is associated with depth information indicating a position of a tomographic plane corresponding to each position in a depth direction.

According to still yet another aspect of the invention, there is provided an image display method including: generating a pseudo two-dimensional image from a plurality of tomographic images of the same subject; displaying at least one of the pseudo two-dimensional image and the plurality of tomographic images; and creating a depth map in which each position on the pseudo two-dimensional image is associated with depth information indicating a position of a tomographic plane corresponding to each position in a depth direction.

In addition, a program may be provided which causes a computer to perform the image display method and another image display method according to the invention.

According to the invention, when at least one of a two-dimensional radiological image and a plurality of tomographic images of the same subject is displayed, a depth map in which each position on the two-dimensional radiological image is associated with depth information indicating a position of a tomographic plane corresponding to each position in a depth direction is created. Therefore, when image diagnosis is performed with reference to both the two-dimensional radiological image and the tomographic images, first, it is possible to easily designate the position of a lesion with reference to the two-dimensional radiological image. In addition, it is possible to rapidly specify the tomographic image of the tomographic plane corresponding to the designated position of the lesion, with reference to the depth map. Therefore, it is possible to rapidly display a specified tomographic image together with the two-dimensional radiological image. As a result, it is possible to perform image diagnosis with high efficiency, with reference to both the two-dimensional radiological image and the tomographic images.

BRIEF DESCRIPTION OF THE DRAWINGS

FIG. 1 is a diagram schematically illustrating a radiography apparatus to which an image display device according to a first embodiment of the invention is applied.

FIG. 2 is a diagram illustrating an arm unit of the radiography apparatus illustrated in FIG. 1, as viewed from the right direction of FIG. 1.

FIG. 3 is a block diagram schematically illustrating the internal structure of a computer of the radiography apparatus illustrated in FIG. 1.

FIG. 8 is a flowchart illustrating a process in the first embodiment.

FIG. 9 is a flowchart illustrating an image display process in the first embodiment.

FIG. 17 is a block diagram schematically illustrating the internal structure of a computer in a third embodiment.

FIG. 18 is a flowchart illustrating a depth map creation process in the third embodiment.

DESCRIPTION OF THE PREFERRED EMBODIMENTS

Figure 4:
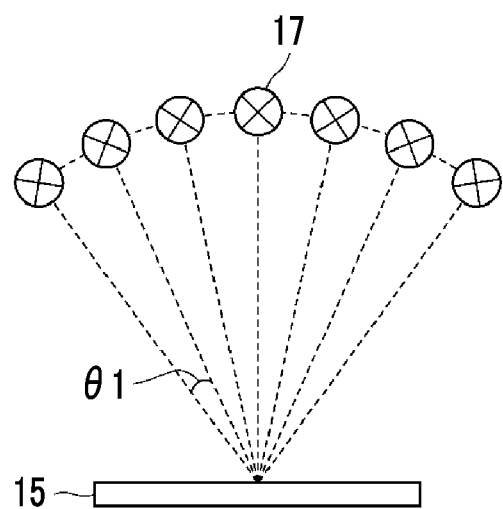
FIG. 4 is a diagram illustrating a plurality of imaging directions.

Hereinafter, embodiments of the invention will be described with reference to the drawings. FIG. 1 is a diagram schematically illustrating the structure of a radiography apparatus to which an image display device according to a first embodiment of the invention is applied. A radiography apparatus 1 is a mammography apparatus which captures the images of the breast M in different imaging directions to acquire a plurality of radiological images in order to generate a two-dimensional radiological image using simple mammography and to generate a tomographic image using breast tomosynthesis imaging. As illustrated in FIG. 1, the radiography apparatus 1 includes an imaging unit 10, a computer 2 connected to the imaging unit 10, and a monitor 3 and an input unit 4 which are connected to the computer 2.

The imaging unit 10 includes a base 11, a rotating shaft 12 which is movable in the vertical direction (Z direction) with respect to the base 11 and is rotatable, and an arm unit 13 which is connected to the base 11 by the rotating shaft 12. FIG. 2 illustrates the arm unit 13, as viewed from the right direction (Y direction) of FIG. 1.

The arm unit 13 has a C-shape and has one end 13A to which a photographing stand 14 is attached and the other end 13B to which a radiation emitting unit 16 is attached so as to face the photographing stand 14. The arm unit 13 is configured such that the end 13A to which the photographing stand 14 is attached and the end 13B to which the radiation emitting unit 16 is attached can be integrally rotated and only the end 13B to which the radiation emitting unit 16 is attached can be rotated. Therefore, the photographing stand 14 and the radiation emitting unit 16 can be integrally rotated. In addition, the photographing stand 14 can be fixed and only the radiation emitting unit 16 can be rotated. In FIG. 2, when the clockwise direction in FIG. 2 is a positive direction, a rotation angle at a rotation position where the arm unit 13 is parallel to the base 11 is 0 degrees and the state of the arm unit 13 when the photographing stand 14 and the radiation emitting unit 16 are integrally rotated θ0 degrees in the clockwise direction is indicated by a virtual line. The rotation and vertical movement of the arm unit 13 are controlled by an arm controller 31 which is incorporated into the base 11.

The photographing stand 14 includes a radiation detector 15, such as a flat panel detector, and a detector controller 33 which controls the reading of a charge signal from the radiation detector 15.

In addition, the photographing stand 14 includes, for example, a circuit board provided with a charge amplifier that converts the charge signal read from the radiation detector 15 into a voltage signal, a correlated double sampling circuit that samples the voltage signal output from the charge amplifier, and an A/D converter that converts the voltage signal into a digital signal.

The radiation detector 15 can repeatedly record and read radiographic images and may be a direct radiation detector that directly receives radiation and generates charge or may be an indirect radiation detector that converts radiation into visible light and then converts the visible light into a charge signal. As a method of reading a radiological image signal, it is preferable to use a thin film transistor (TFT) reading method of turning on or off a TFT switch to read the radiological image signal or an optical reading method of emitting reading light to read the radiological image signal. However, the reading method is not limited thereto and other methods may be used.

The radiation emitting unit 16 includes a radiation source 17 and a radiation source controller 32. The radiation source controller 32 controls the emission time of radiation from the radiation source 17 and the radiation generation conditions (for example, a tube current, time, and a tube current-time product) of the radiation source 17.

In addition, a compression plate 18 that is provided above the photographing stand 14 and compresses the breast, a supporting portion 20 that supports the compression plate 18, and a moving mechanism 19 that moves the supporting portion 20 in the vertical direction (Z direction) are provided at the center of the arm unit 13. The position and compression pressure of the compression plate 18 are controlled by a compression plate controller 34.

The computer 2 includes, for example, a central processing unit (CPU) and a storage device, such as a semiconductor memory, a hard disk, or an SSD. A control unit 21, a radiological image storage unit 22, a reconstruction unit 23, a depth map creation unit 24, a display control unit 25, and a storage unit 26 shown in FIG. 3 are formed by these hardware components.

The control unit 21 outputs predetermined control signals to various types of controllers 31 to 34 to control the overall operation of the device.

The radiological image storage unit 22 stores a plurality of radiological images which are generated by an imaging operation that is performed in a predetermined imaging direction while rotating both ends 13A and 13B of the arm unit 13 and are then detected by the radiation detector 15. The image of the breast M is captured in the following directions: cranio-caudal (CC) imaging which emits radiation from the top to capture an image; medial-lateral (ML) imaging which emits radiation from the side to capture an image; and mediolateral-oblique (MLO) imaging which emits radiation in an oblique direction to capture an image. The arm unit 13 is rotated to perform positioning according to the imaging direction and then imaging is performed. FIG. 1 illustrates positioning when cranio-caudal (CC) imaging is performed. In this embodiment, it is not necessary to perform all of the CC imaging, the ML imaging, and the MLO imaging and at least one of the CC imaging, the ML imaging, and the MLO imaging may be performed.

In this embodiment, as illustrated in FIG. 4, only the end 13B to which the radiation emitting unit 16 is attached is rotated and imaging is performed in a plurality of imaging directions which are arranged at predetermined angular intervals of θ1, that is, tomosynthesis imaging is performed. The radiation detector 15 detects a plurality of radiological images and the plurality of radiological images are also stored. In this embodiment, tomosynthesis imaging is performed in each of the above-mentioned imaging directions to acquire a plurality of radiological images and the tomographic images of the breast M generated from the plurality of radiological images and a two-dimensional radiological image acquired by simple imaging are displayed.

Figure 5:
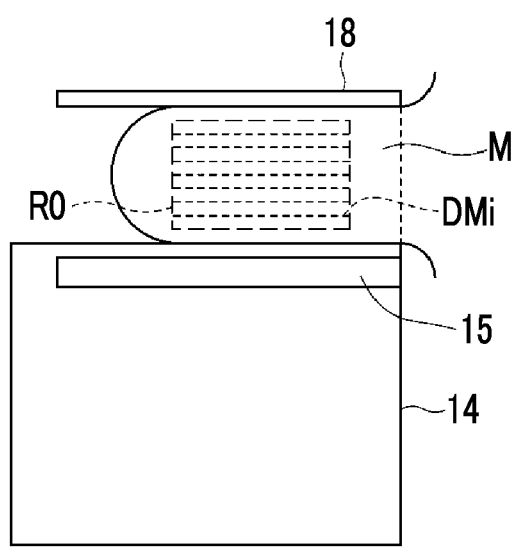
FIG. 5 is a diagram illustrating a reconstruction range of a tomographic image.

The reconstruction unit 23 reconstructs a plurality of radiological images stored in the radiological image storage unit 22 to generate a tomographic image in which a desired tomographic plane of the breast M is emphasized. Specifically, the reconstruction unit 23 reconstructs the radiological images using a back projection method, such as a simple back projection method or a filtered back projection method, to generate a tomographic image. In addition, as illustrated in FIG. 5, the reconstruction unit 23 generates tomographic images in a plurality of desired tomographic planes DMi (i=1 to n, n is the number of tomographic planes) parallel to a detection surface of the radiation detector 15 in a predetermined reconstruction range R0 in the breast M.

Figure 6:
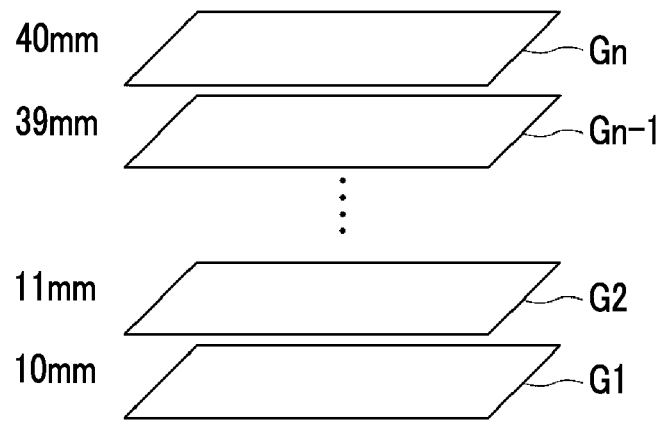
FIG. 6 is a diagram illustrating the creation of a depth map.

The depth map creation unit 24 creates a depth map in which each position on the two-dimensional radiological image that is acquired in each of the imaging directions is associated with depth information indicating the position of the tomographic plane corresponding to each position from a reference position in the depth direction. FIG. 6 is a diagram illustrating the creation of the depth map. In this embodiment, as described above, a plurality of tomographic images Di (i=1 to n, n is the number of tomographic planes) and one two-dimensional radiological image G0 are stored in the radiological image storage unit 22 for one imaging direction. In this embodiment, for example, the gap between the tomographic planes is 1 mm and the tomographic images Di are generated in the tomographic planes DMi which are arranged at an interval of 1 mm in the depth range of 10 mm to 40 mm from the reference position, which is the detection surface of the radiation detector 15, in the direction of the radiation source 17. However, the invention is not limited thereto.

The depth map creation unit 24 divides the two-dimensional radiological image G0 into a plurality of areas and calculates the correlation between each of the divided areas and the plurality of tomographic images Di. For example, as illustrated in FIG. 6, the depth map creation unit 24 divides the two-dimensional radiological image G0 into 6×8 areas and calculates the correlation between one area A1 among the divided areas and the plurality of tomographic images Di. Then, the depth map creation unit 24 creates a depth map in which the depth of the tomographic plane of the tomographic image Di including an area with the highest correlation from the reference position is associated with the position of the area A1. For example, when the depth of the tomographic image including the area which has the highest correlation with the area A1 in FIG. 5 is 30 mm, a depth map MP in which 30 mm is associated with the position of the area A1 is created. In addition, in the depth map MP, an area of the two-dimensional radiological image G0 in which the breast M is not included may be associated with a predetermined depth (for example, 10 mm). The created depth map MP is stored in the storage unit 26.

The depth map MP is created by associating the position of each area on the two-dimensional radiological image G0 with the depth information indicating the position of the tomographic plane corresponding to the position of each area in the depth direction. However, the depth map MP may be created by associating the position of each pixel on the two-dimensional radiological image with depth information indicating the position of the tomographic plane corresponding to the position of each pixel in the depth direction. In this case, a depth map may be created by setting an area which has a predetermined size and has a target pixel on the two-dimensional radiological image as the center, calculating the correlation between the area and the tomographic image Di, and associating the depth of the tomographic plane of the tomographic image Di including an area with the highest correlation from the reference position with the position of a target pixel where the area is set.

The positional relationship between the radiation source 17 and the radiation detector 15 when the two-dimensional radiological image G0 is acquired and when the plurality of tomographic images Di are reconstructed is known. Therefore, the position of each pixel on the two-dimensional radiological image G0 may be associated with depth information indicating the position of the tomographic plane corresponding to the position of each pixel in the depth direction, on the basis of the positional relationship between the radiation source 17 and the radiation detector 15, to create the depth map MP. In this case, it is possible to specify a projection line of radiation which passes through a given pixel position on the two-dimensional radiological image G0, from the positional relationship between the given pixel position, the radiation source 17, and the radiation detector 15. When the projection line can be specified, it is possible to specify a position on the tomographic image Di which the projection line passes through. Then, for example, the position of the tomographic plane of a tomographic image with the maximum pixel value in the depth direction among the plurality of tomographic images Di on the projection line may be associated with the pixel position which the projection line passes through to create the depth map MP.

The display control unit 25 displays the two-dimensional radiological image captured in the instructed imaging direction on the monitor 3, in response to an instruction from the input unit 4. Then, the display control unit 25 displays the tomographic image on the monitor 3 with reference to the depth map MP, in response to an instruction from the input unit 4. The display of the tomographic image will be described below.

In the above-mentioned example, the two-dimensional radiological image G0 is divided into 6×8 areas. However, for example, the two-dimensional radiological image G0 may be divided into areas with a predetermined size, such as a size of 10 pixels×10 pixels or a size of 1 cm×1 cm. In addition, a known area extraction process may be performed for the two-dimensional radiological image G0 such that the breast M is divided into a plurality of anatomic areas (for example, a breast area and a breast muscle area, or a lesion and the mammary gland). In this case, the depth map MP may be created as follows: the depth of each area in the depth map MP is calculated for each pixel included in each area and the mean or mode of the calculated depths in each area is set to the depth of the area.

The monitor 3 is a known display device, such as a CRT or a liquid crystal display, and displays the two-dimensional radiological image G0 and the tomographic images Di output from the computer 2.

The input unit 4 is a keyboard or a pointing device, such as a mouse, and receives, for example, an imaging condition or an imaging start instruction input from an operator.

Next, a process in the first embodiment will be described. FIG. 8 is a flowchart illustrating an imaging process in the first embodiment. First, the imaging direction is set by an instruction from the input unit 4 (Step ST1). Specifically, first, the imaging control unit 21 outputs information about the imaging direction instructed from the input unit 4 to the arm controller 31. The arm controller 31 outputs a control signal such that the arm unit 13 is located at a position corresponding to the designated imaging direction with respect to the base 11. Then, the arm unit 13 is rotated integrally with the photographing stand 14 and the radiation emitting unit 16 on the basis of the control signal output from the arm controller 31. When the arm unit 13 is located at the position corresponding to the designated imaging direction, the arm controller 31 stops the arm unit 13. In this way, the imaging direction is set. Then, the breast M of the patient is placed on the photographing stand 14 and is compressed with a predetermined pressure by the compression plate 18 (Step ST2). Then, after various imaging conditions are input through the input unit 4, an imaging start instruction is input through the input unit 4.

When an imaging start instruction is input through the input unit 4, simple imaging is performed to acquire a two-dimensional radiological image (Step ST3). Specifically, the control unit 21 outputs control signals to the radiation source controller 32 and the detector controller 33 such that radiation is emitted and a radiological image signal is read, in response to the imaging start instruction. In response to the control signals, the radiation source 17 emits radiation, the radiation detector 15 detects the radiological image of the breast M, and the detector controller 33 reads a radiological image signal from the radiation detector 15. Then, predetermined signal processing is performed for the radiological image signal and the radiological image signal is stored as the two-dimensional radiological image in the radiological image storage unit 22 of the computer 2.

Then, tomosynthesis imaging is performed (Step ST4). The tomosynthesis imaging is performed as follows: the photographing stand 14 is fixed; and the breast M is irradiated with radiation while the radiation emitting unit 16 is rotated with respect to the photographing stand 14 by the arm unit 13. Specifically, first, the control unit 21 reads an angle $\theta 1$ for determining a predetermined imaging interval and outputs information about the read angle $\theta 1$ to the arm controller 31.

Then, the arm controller 31 receives the information about the angle $\theta 1$ output from the control unit 21. First, the arm controller 31 outputs a control signal such that the end of the arm unit 13 to which the radiation emitting unit 16 is attached is located at an initial position where the inclination angle of the end with respect to the photographing stand 14 is the maximum.

Then, the control unit 21 outputs control signals to the radiation source controller 32 and the detector controller 33 such that radiation is emitted and the radiological image signal is read, in response to the control signal output from the arm controller 31, with the arm unit 13 located at the initial position. In response to the control signals, the radiation source 17 emits radiation, the radiation detector 15 detects the radiological image of the breast M captured at the initial position, and the detector controller 33 reads the radiological image signal from the radiation detector 15. Then, predetermined signal processing is performed for the radiological image signal and the radiological image signal is stored as a radiological image for creating a tomographic image in the radiological image storage unit 22 of the computer 2.

Then, the arm controller 31 outputs a control signal such that the arm unit 13 is rotated $\theta 1$ degrees from the initial position. That is, in this embodiment, the arm controller 31 outputs a control signal such that the arm unit 13 is rotated $\theta 1$ degrees in a direction from the initial position to an end position where the final imaging process is performed. Then, with the arm unit 13 rotated $\theta 1$ degrees in response to the control signal output from the arm controller 31, the control unit 21 outputs control signals to the radiation source controller 32 and the detector controller 33 such that radiation is emitted and the radiological image signal is read.

Specifically, the control unit 21 outputs control signals to the radiation source controller 32 and the detector controller 33 such that radiation is emitted and the radiological image is read. In response to the control signals, the radiation source 17 emits radiation, the radiation detector 15 detects the radiological image of the breast M captured at the position to which the breast M has been moved θ1 degrees from the initial position, and the detector controller 33 reads the radiological image signal. Then, predetermined signal processing is performed for the radiological image signal and the radiological image signal is stored as a radiological image in the radiological image storage unit 22 of the computer 2.

The above-mentioned process is repeatedly performed until the arm unit 13 is rotated to the end position and a plurality of radiological images are stored in the radiological image storage unit 22.

Then, the reconstruction unit 23 reconstructs a plurality of radiological images in the reconstruction range of the tomographic image of the breast M to generate a plurality of tomographic images Di (Step ST5). The plurality of tomographic images Di are stored in the radiological image storage unit 22. The imaging process is repeatedly performed for the left and right breasts M in all of the predetermined imaging directions until the two-dimensional radiological image G0 and the tomographic images Di are generated.

Then, the depth map creation unit 24 creates the depth map MP in which each position on the two-dimensional radiological image acquired in each of the imaging directions is associated with the depth information indicating the position of the tomographic plane corresponding to each position in the depth direction (Step ST6) and ends the process. The created depth map MP is stored in the storage unit 26.

FIG. 9 is a flowchart illustrating an image display process in the first embodiment. When an imaging direction designation and image display instruction is input through the input unit 4, the display control unit 25 reads the two-dimensional radiological image G0 captured in the designated imaging direction from the radiological image storage unit 22 and displays the two-dimensional radiological image G0 on the monitor 3 (Step ST11).

Figure 7:
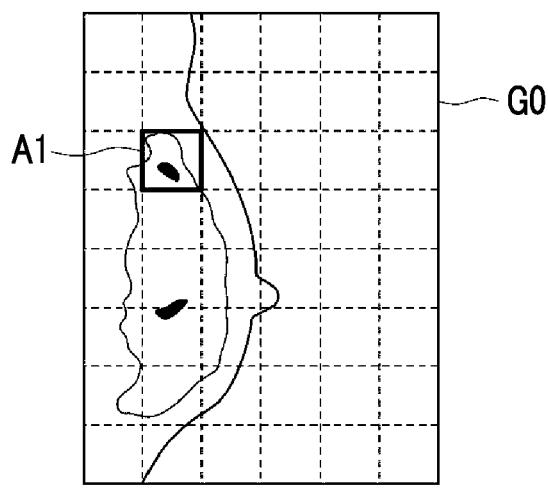
FIG. 7 is a diagram illustrating the depth map.
Figure 10:
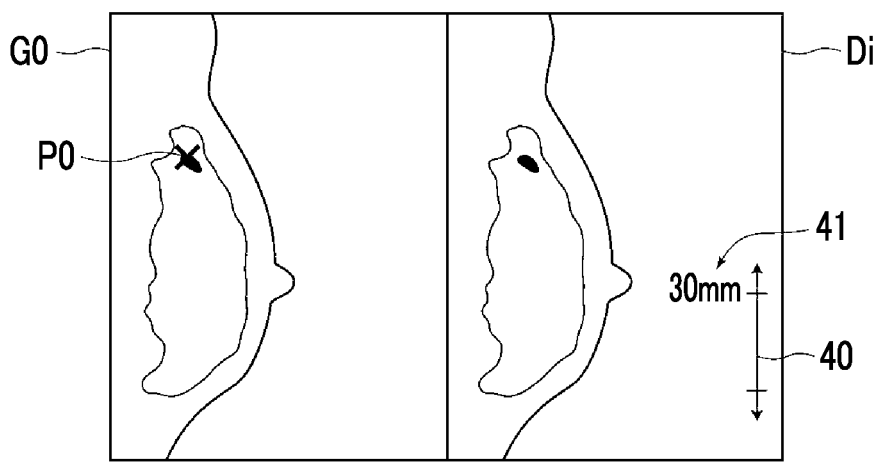
FIG. 10 is a diagram illustrating an example of an image displayed on a monitor.

Then, when a position on the two-dimensional radiological image G0 is designated through the input unit 4 (Step ST12), the display control unit 25 acquires depth information corresponding to the designated position on the two-dimensional radiological image G0, with reference to the depth map MP (Step ST13), displays the tomographic image Di of the tomographic plane corresponding to the acquired depth information on the monitor 3 (Step ST14), and ends the process. FIG. 10 is a diagram illustrating an image displayed on the monitor 3. As illustrated in FIG. 10, the two-dimensional radiological image G0 is displayed on the left area of the screen of the monitor 3 and the tomographic image Di corresponding to a designated position P0 on the two-dimensional radiological image G0 is displayed in the vicinity of the two-dimensional radiological image G0, specifically, in an area on the right side of the two-dimensional radiological image G0. For example, when the designated position on the two-dimensional radiological image G0 corresponds to the area which is surrounded by a thick line in the depth map illustrated in FIG. 7, the tomographic image of the tomographic plane corresponding to a depth of 30 mm is displayed on the monitor 3 since the depth from the reference position is 30 mm. At that time, the tomographic planes to be displayed may be sequentially switched in response to an instruction from the input unit 4 and the tomographic images may be displayed as a moving image in which the tomographic planes are sequentially switched. A scale 40 indicating the position of the tomographic plane that is being displayed among all of the tomographic planes in the depth direction and a value 41 indicating the depth of the tomographic plane are both displayed on the displayed tomographic image Di.

Figure 11:
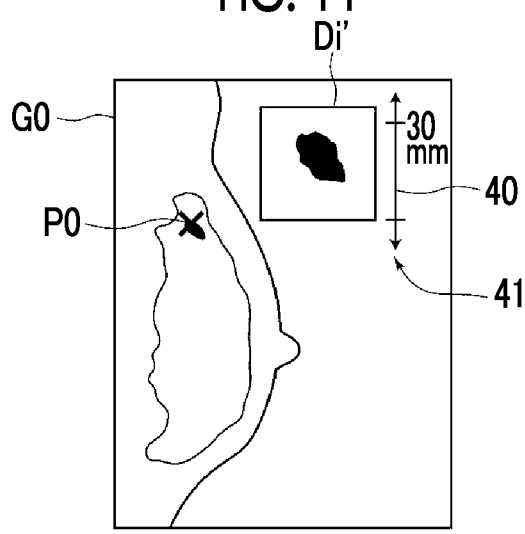
FIG. 11 is a diagram illustrating an example of the image displayed on the monitor.

As illustrated in FIG. 11, an area in a predetermined range including the designated position on the two-dimensional radiological image G0 may be cut out from the corresponding tomographic image Di and a cut tomographic image Di' may be displayed so as to be superimposed on the two-dimensional radiological image G0. In this case, the tomographic image Di' may be displayed as a moving image, or both the scale 40 indicating the position of the tomographic plane in the depth direction and the value 41 indicating the depth of the tomographic plane may be displayed.

Figure 12:
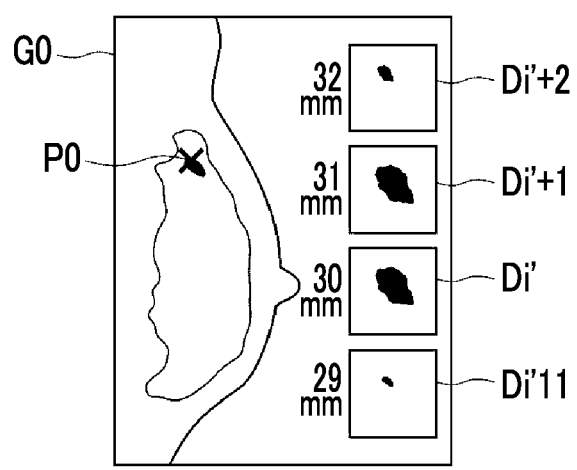
FIG. 12 is a diagram illustrating an example of the image displayed on the monitor.

As illustrated in FIG. 12, an area in a predetermined range including the designated position on the two-dimensional radiological image G0 may be cut out from the corresponding tomographic image Di. In addition, an area corresponding to the cut area may be cut out from the tomographic images of a plurality of tomographic planes which are arranged before and after the tomographic plane corresponding to the designated position. Then, the tomographic images Di'+2, Di'+1, Di', and Di'-1 of a plurality of cut tomographic planes may be displayed in a line. In this case, a value indicating the depth of the plurality of tomographic planes may also be displayed. In this case, in addition to adjacent tomographic planes, the tomographic planes to be displayed may be arranged at a predetermined interval (for example, 5 mm).

As such, in this embodiment, the depth map MP in which each position on the two-dimensional radiological image is associated with the depth information indicating the position of the tomographic plane corresponding to each position in the depth direction is created. Therefore, when image diagnosis is performed with reference to both the two-dimensional radiological image G0 and the tomographic image Di, first, the two-dimensional radiological image G0 is referred to, which makes it easy to designate the position of the lesion. In addition, the reference of the depth map MP makes it possible to rapidly specify the tomographic image Di of the tomographic plane corresponding to the position of the designated lesion. Therefore, it is possible to rapidly display a specified tomographic image Di together with the two-dimensional radiological image G0. As a result, it is possible to perform image diagnosis with high efficiency with reference to both the two-dimensional radiological image G0 and the tomographic image Di.

The two-dimensional radiological image G0 is divided into a plurality of areas and the depth map MP in which the position of each area on the two-dimensional radiological image G0 is associated with the depth information of the position of each area is created. Therefore, when the operator designates the position of the area of interest, it is possible to stably display the tomographic image of a desired tomographic plane even though a position is roughly designated.

In the above-described embodiment, the two-dimensional radiological image G0 and the tomographic image Di are acquired at the same time. However, for example, in health examination, when the result of diagnosis using the two-dimensional radiological image G0 shows that thorough medical examination is required and a tomographic image is acquired by tomosynthesis imaging in the thorough medical examination, the two-dimensional radiological image G0 and the tomographic image Di are captured at different times. As a result, the geometric shape of the breast M included in the two-dimensional radiological image G0 is different from that of the breast M included in the tomographic image Di due to, for example, a difference in the degree of compression or a minute difference in the imaging position. In this case, the positional relationship between the two-dimensional radiological image G0 and the depth map MP varies. As a result, there is a concern that each position on the two-dimensional radiological image G0 will not be operatively associated with the depth information corresponding to each position. Next, a method for solving this problem will be described as a second embodiment.

Figure 13:
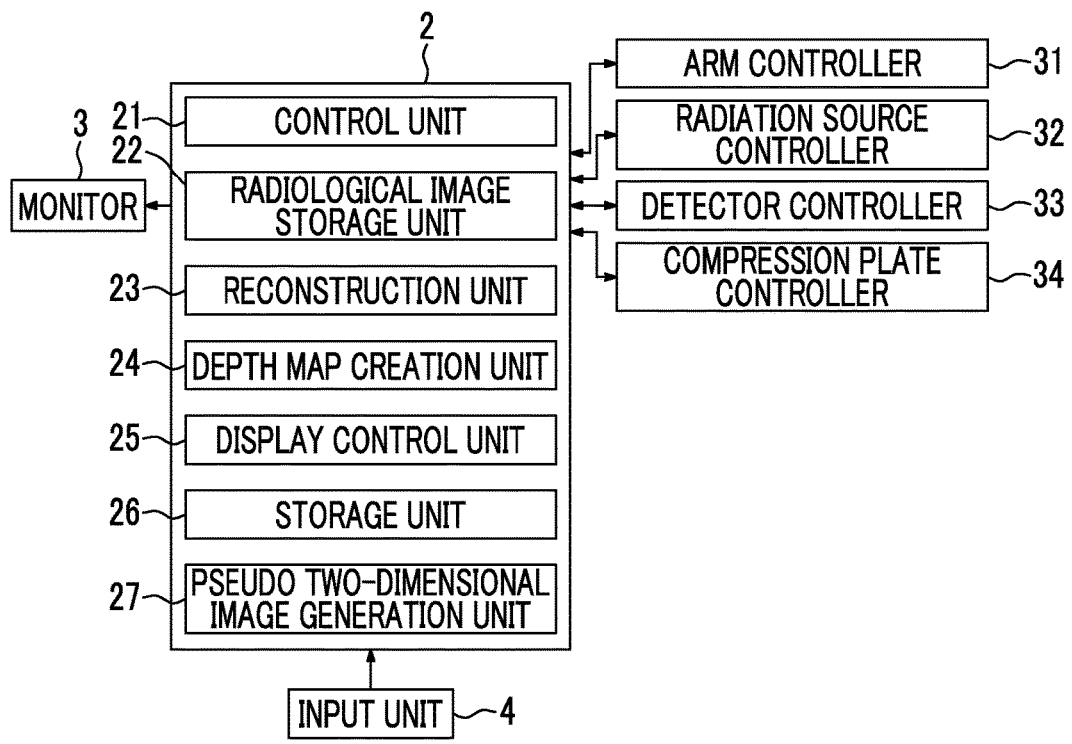
FIG. 13 is a block diagram schematically illustrating the internal structure of a computer in a second embodiment.

FIG. 13 is a block diagram schematically illustrating the internal structure of a computer according to the second embodiment. In the second embodiment, the same components as those in the first embodiment are denoted by the same reference numerals and the detailed description thereof will not be repeated. An image processing device according to the second embodiment differs from the image processing device according to the first embodiment in that it further includes a pseudo two-dimensional image generation unit 27 and the depth map creation unit 24 creates a depth map MP in which a pseudo two-dimensional image is associated with a two-dimensional radiological image G0.

Figure 14:
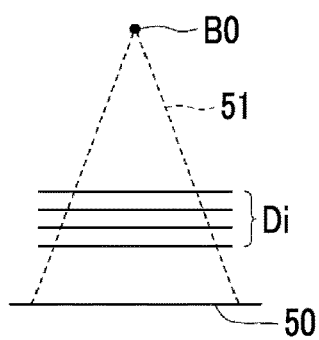
FIG. 14 is a diagram illustrating the generation of an MIP image.

The pseudo two-dimensional image generation unit 27 generates a pseudo two-dimensional image from a plurality of tomographic images Di generated by the reconstruction unit 23. In this embodiment, the pseudo two-dimensional image generation unit 27 generates a maximum intensity projection (MIP) image as the pseudo two-dimensional image from the plurality of tomographic images Di, using an MIP method. FIG. 14 is a diagram illustrating the generation of the MIP image. As illustrated in FIG. 14, the position of the radiation source 17 when the end of the arm unit 13 to which the radiation emitting unit 16 is attached is located at a rotation position where it is perpendicular to the radiation detector 15 is used as a reference point B0 of projection and the position of the radiation detector 15 is located on a projection surface 50. In this case, the pseudo two-dimensional image generation unit 27 projects a plurality of tomographic images Di from the reference point B0 to the projection surface 50. In this case, the maximum pixel value of a projection line 51 becomes the pixel value of the MIP image projected to the projection surface 50. The generated MIP image, that is, the pseudo two-dimensional image is stored in the radiological image storage unit 22. In this embodiment, the tomographic image Di is created on the assumption that radiation is a fan beam. However, when a pseudo two-dimensional image is created, the coordinate system of the tomographic image Di may be converted into a coordinate system assuming parallel projection.

Figure 15:
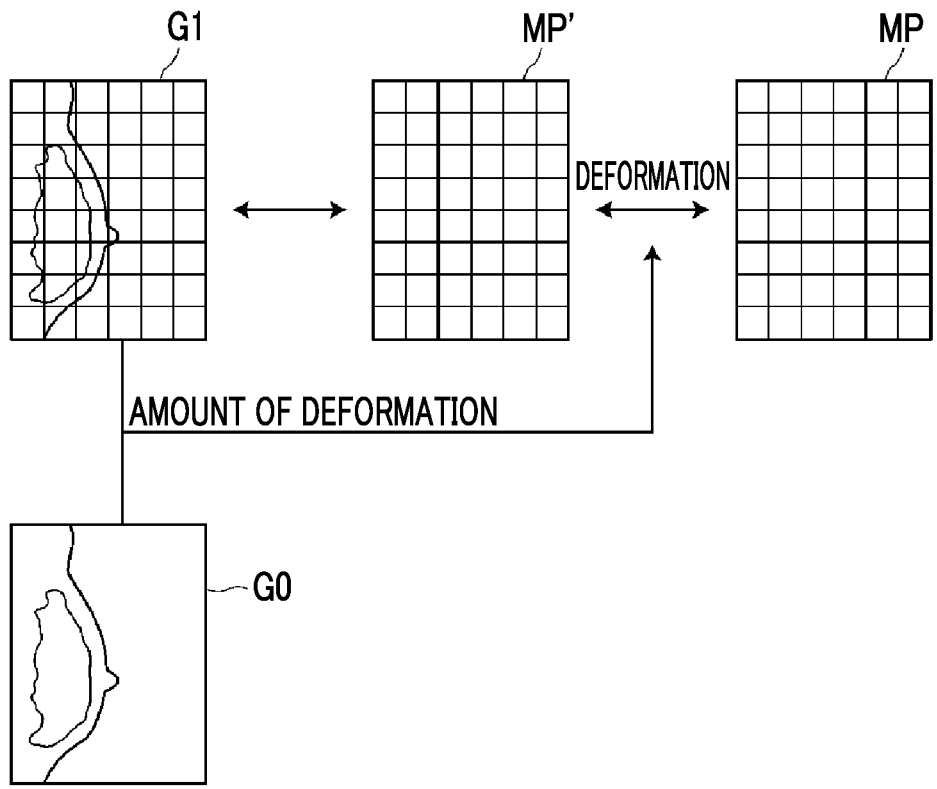
FIG. 15 is a diagram illustrating the creation of a depth map in the second embodiment.

FIG. 15 is a diagram illustrating the creation of a depth map in the second embodiment. The value of each pixel in an MIP image G1 is the maximum value in a plurality of tomographic images Di on projection lines corresponding to each pixel. Therefore, each pixel of the MIP image G1 can be associated with the depth of the tomographic image Di from which the value of each pixel is acquired. In the second embodiment, as illustrated in FIG. 15, first, the depth map creation unit 24 creates a temporary depth map MP' in which each position on the MIP image G1 is associated with depth information indicating the position of the tomographic plane corresponding to each position in the depth direction. In FIG. 15, 6×8 pixels are provided for convenience of explanation.

As described above, when the two-dimensional radiological image G0 and the tomographic images Di stored in the radiological image storage unit 22 are captured at different times, the geometric shapes of the breast M included in the images are different from each other due to, for example, a difference in the degree of compression and a minute difference in the position of the breast M to be compressed. Therefore, in the second embodiment, the depth map creation unit 24 calculates the amount of deformation of the MIP image G1 such that the breast M included in the MIP image G1 and the breast M included in the two-dimensional radiological image G0 have the same geometric shape. Here, rotation, scaling, and translation parameters of affine transformation can be used as the amount of deformation. Specifically, the depth map creation unit 24 may calculate the amount of deformation for aligning the scan lines of the breast M and the amount of deformation for aligning other positions on the basis of a feature point on the image (for example, a nipple, a mammary gland, and calcification). In addition, the depth map creation unit 24 may perform template matching between the two-dimensional radiological image G0 and the MIP image G1 to calculate the amount of deformation.

Then, the depth map creation unit 24 deforms the temporary depth map MP', using the calculated amount of deformation, to create the depth map MP. Therefore, each position on the two-dimensional radiological image G0 is associated with each position of the depth map MP.

Figure 16:
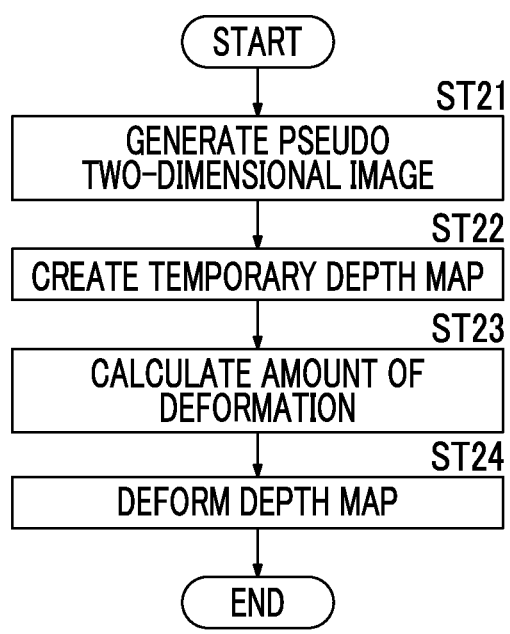
FIG. 16 is a flowchart illustrating a depth map creation process in the second embodiment.

Next, a process in the second embodiment will be described. A process of acquiring the two-dimensional radiological image G0 and the tomographic image Di and an image display process are the same as those in the first embodiment. Therefore, in the second embodiment, only a depth map creation process will be described. FIG. 16 is a flowchart illustrating the depth map creation process in the second embodiment. First, the pseudo two-dimensional image generation unit 27 generates a pseudo two-dimensional image (MIP image G1) from a plurality of tomographic images Di (Step ST21). Then, the depth map creation unit 24 creates the temporary depth map MP' in which each position on the pseudo two-dimensional image is associated with the depth information indicating the position of the tomographic plane corresponding to each position in the depth direction (Step ST22). Then, the depth map creation unit 24 calculates the amount of deformation of the pseudo two-dimensional image such that the breast M included in the pseudo two-dimensional image and the breast M included in the two-dimensional radiological image G0 have the same geometric shape (Step ST23), deforms the temporary depth map MP' on the basis of the amount of deformation to create the depth map MP (Step ST24), and ends the process.

As such, in the second embodiment, the pseudo two-dimensional image is generated from the plurality of tomographic images Di and the temporary depth map MP' in which each position on the pseudo two-dimensional image is associated with the depth information indicating the position of the tomographic plane corresponding to each position in the depth direction is created. Then, the temporary depth map MP' is deformed, on the basis of the corresponding positional relationship between each position on the two-dimensional radiological image G0 and each position on the pseudo two-dimensional image, to create the depth map MP. Therefore, as described above, even when the breast M included in the two-dimensional radiological image G0 and the breast M included in the tomographic image Di have different geometric shapes due to a difference in imaging time, it is possible to reliably associate each position on the two-dimensional radiological image with the tomographic plane.

In the second embodiment, the amount of deformation of the pseudo two-dimensional image is calculated such that the breast M included in the pseudo two-dimensional image and the breast M included in the two-dimensional radiological image G0 have the same geometric shape, and the temporary depth map MP' is deformed on the basis of the calculated amount of deformation. However, the correspondence relationship between the pixels of the pseudo two-dimensional image and the two-dimensional radiological image G0 may be calculated by, for example, template matching and the depth map MP including the correspondence relationship and the temporary depth map MP' may be created. In this case, when a position on the displayed two-dimensional radiological image G0 is designated, first, a position on the pseudo two-dimensional image is detected from the correspondence relationship between the pixels of the pseudo two-dimensional image and the two-dimensional radiological image G0 in the depth map MP. Then, the depth information of a position corresponding to the detected position on the pseudo two-dimensional image is acquired from the temporary depth map MP' in the depth map MP. Then, the tomographic image of the tomographic plane corresponding to the depth information is read from the radiological image storage unit 22 and is then displayed on the monitor 3.

In the second embodiment, the created temporary depth map MP' may be used as the depth map MP. In this case, instead of the two-dimensional radiological image G0, the pseudo two-dimensional image may be used for display.

In some cases, the following method is used in order to reduce the exposure dose of the subject or to shorten the imaging time: the two-dimensional radiological image G0 is not captured; a pseudo two-dimensional image, such as an MIP image, is generated from a tomographic image acquired by tomosynthesis imaging; and the pseudo two-dimensional image is used as the two-dimensional radiological image G0 for image diagnosis. However, in the tomosynthesis imaging, the emission angle of radiation is limited. Therefore, even when a projection image is simply superimposed by, for example, the back projection method to reconstruct the tomographic image, the virtual image of a structure is likely to be captured in an area in which no structure is inherently present. Specifically, in some cases, the image of an artifact is captured in the area in which no structure is originally present in the tomographic image of the tomographic plane that is different from the tomographic image of the tomographic plane in which a structure is present by back projection. When the artifact is too conspicuous, it is difficult to check a structure required to be diagnosed, for example, a lesion. In addition, the same problem as described above also occurs even in a case in which the tomographic image is reconstructed by methods other than the back projection method. Therefore, the pseudo two-dimensional image generated from the tomographic image is not suitable for image diagnosis. Next, a method for solving this problem will be described as a third embodiment.

FIG. 17 is a block diagram schematically illustrating the internal structure of a computer according to the third embodiment. In the third embodiment, the same components as those in the first embodiment are denoted by the same reference numerals and the detailed description thereof will not be repeated. An image processing device according to the third embodiment differs from the image processing device according to the first embodiment in that it includes a first reconstruction unit 23A, a second reconstruction unit 23B, and a pseudo two-dimensional image generation unit 27, the first reconstruction unit 23A reconstructs a tomographic image Di suitable for display, a second reconstruction unit 23B generates a tomographic image DHi suitable to generate a pseudo two-dimensional image for display, and the pseudo two-dimensional image generation unit 27 generates the pseudo two-dimensional image using the tomographic image DHi suitable to generate the pseudo two-dimensional image.

Here, the tomographic image DHi suitable to generate the pseudo two-dimensional image for display can be generated by any known method, such as a reconstruction method disclosed in JP2005-152658A which is different from that for acquiring the tomographic image Di, calculates a plurality of non-uniform weighting coefficients used for a back projection process, and performs back projection for a plurality of radiological images using the non-uniform weighting coefficients. In addition, a method may be used which performs frequency processing for attenuating a low-frequency component of a radiological image, which is acquired by image capture at an irradiation position where an incident angle is equal to or greater than a given value, relative to a high-frequency component to reconstruct a tomographic image.

Next, a process in the third embodiment will be described. In the third embodiment, the two-dimensional radiological image G0 is not acquired and an image display process is the same as that in the first embodiment. Therefore, in this embodiment, only a depth map creation process will be described. FIG. 18 is a flowchart illustrating the depth map creation process in the third embodiment.

First, the first reconstruction unit 23A reconstructs a plurality of radiological images acquired by tomosynthesis imaging to generate tomographic images Di for display (Step ST31). At that time, a process suitable for display is performed as the reconstruction. The second reconstruction unit 23B reconstructs a plurality of radiological images acquired by tomosynthesis imaging to generate tomographic images DHi for generating a pseudo two-dimensional image (Step ST32). At that time, a process suitable for generating the pseudo two-dimensional image is performed as the reconstruction.

Then, the pseudo two-dimensional image generation unit 27 generates an MIP image as the pseudo two-dimensional image from a plurality of tomographic images DHi using a maximum intensity projection method (MIP method) (Step ST33). In addition, similarly to the second embodiment, the pseudo two-dimensional image generation unit 27 generates a depth map MP in which each position on the image is associated with depth information indicating the position of the tomographic plane corresponding to each position in the depth direction (Step ST34) and ends the process.

As such, in the third embodiment, the tomographic images DHi for generating a two-dimensional radiological image, which are different from the tomographic images Di for display, are generated and the pseudo two-dimensional image is generated as the two-dimensional radiological image from the tomographic images DHi for generating a two-dimensional radiological image. Therefore, the pseudo two-dimensional image can be suitable for display.

In the above-described embodiment, the operator designates a position on the two-dimensional radiological image G0. However, the position which is considered as the lesion may be automatically detected and the tomographic image of the position may be displayed. This will be described below as a fourth embodiment.

Figure 19:
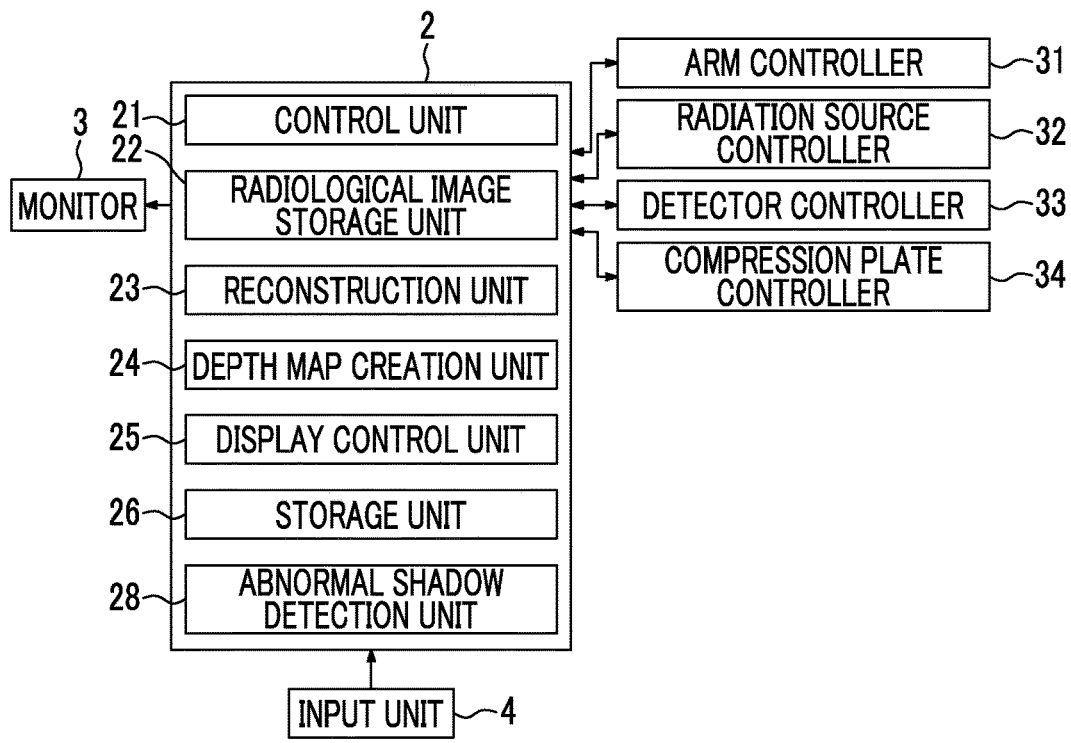
FIG. 19 is a block diagram schematically illustrating the internal structure of a computer in a fourth embodiment.

FIG. 19 is a block diagram schematically illustrating the internal structure of a computer according to the fourth embodiment. In the fourth embodiment, the same components as those in the first embodiment are denoted by the same reference numerals and the detailed description thereof will not be repeated. An image processing device according to the fourth embodiment differs from the image processing device according to the first embodiment in that it includes an abnormal shadow detection unit 28 that detects an abnormal shadow which is considered as the lesion from the two-dimensional radiological image G0.

The abnormal shadow detection unit 28 detects the abnormal shadow from the two-dimensional radiological image G0, using, for example, the following methods: a method which performs image processing for the two-dimensional radiological image G0, using an iris filter, and performs threshold processing for an output value to automatically detect candidates for a tumor shadow (a form of an abnormal shadow) which is a form of, for example, a cancer (see JP1998-97624A (JP-H10-97624A)); or a method which performs image processing, using a morphology filter, and performs threshold processing for an output value to automatically detect candidates for a minute calcified shadow (a form of an abnormal shadow) which is another form of, for example, a breast cancer (see JP 1996-294479A (JP-H08-294479A)).

Figure 20:
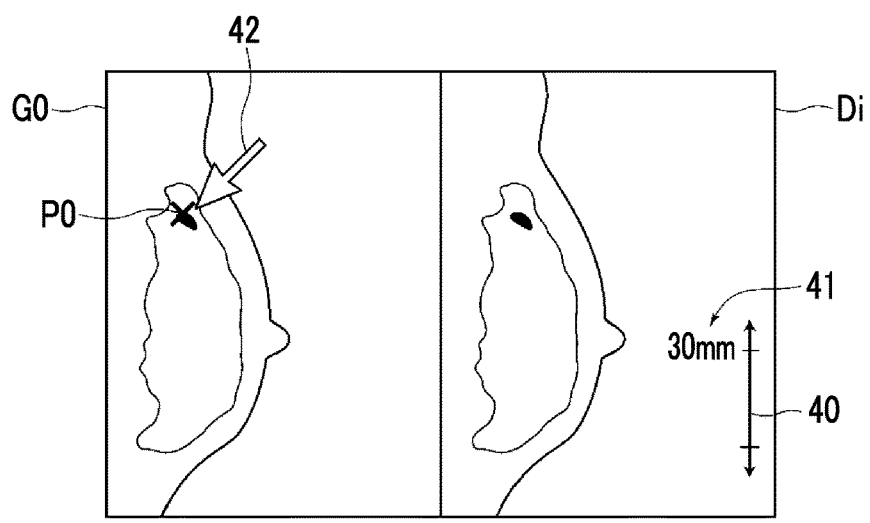
FIG. 20 is a diagram illustrating an example of an image displayed on a monitor in the fourth embodiment.

FIG. 20 illustrates the display of an image when the abnormal shadow is detected. When the two-dimensional radiological image G0 is displayed as illustrated in FIG. 20, an arrow 42 indicating the detected abnormal shadow is given on the two-dimensional radiological image G0, the depth map MP is referred to, and the tomographic image Di of the tomographic plane corresponding to the position of the abnormal shadow is displayed on the right side of the two-dimensional radiological image G0. In this case, the tomographic image Di may be displayed as a moving image, or both a scale 40 indicating the position of the tomographic plane in the depth direction and a value 41 indicating the depth of the tomographic plane may be displayed.

As such, in the fourth embodiment, the abnormal shadow is detected from the two-dimensional radiological image G0. Therefore, the reference of the depth map MP makes it possible to rapidly display the tomographic image Di of the tomographic plane including the abnormal shadow. As a result, it is possible to easily check the abnormal shadow.

In the fourth embodiment, the abnormal shadow is detected from the two-dimensional radiological image G0. However, the depth map MP may be created by calculating the correlation between an area including the detected abnormal shadow and a plurality of tomographic images Di and associating the depth of the tomographic plane of the tomographic image Di, which includes an area with the highest correlation, from the reference position with the position of the area including the abnormal shadow.

In the above-described embodiment, the depth map MP is created so as to be associated with the entire area of the two-dimensional radiological image G0. However, for example, an area including the breast M in the two-dimensional radiological image G0 may be extracted and the depth map MP may be created only for the area including the breast M. As such, when the depth map MP is created only for the area including the breast M, it is possible to shorten the calculation time required to create the depth map MP. In this case, when a position other than the breast M in the displayed two-dimensional radiological image G0 is designated, a warning indicating that there is no tomographic image corresponding to the designated position may be issued, or a tomographic image corresponding to the central tomographic plane among a plurality of tomographic images Di may be displayed.

The depth map MP may be created by a combination of the methods according to each of the above-described embodiments. For example, the accuracy of the depth map MP varies depending on the type (for example, calcification or tumor mass), size, and position of the lesion included in the two-dimensional radiological image G0. Therefore, the abnormal shadow may be detected from the tomographic image Di as in the fourth embodiment. When the abnormal shadow is not included in the tomographic image of the tomographic plane corresponding to a given area of the two-dimensional radiological image G0 in the depth map MP created in the first to third embodiments, the position of the tomographic plane in the depth direction in the depth map MP may be corrected such that the abnormal shadow is included in the tomographic image of the tomographic plane corresponding to the area.

In the above-described embodiment, a plurality of radiological images acquired by tomosynthesis imaging are reconstructed to generate the tomographic image. However, the tomographic image may be generated by CT which arranges the radiation source and the radiation detector so as to face each other, with the subject interposed therebetween, rotates a set of the radiation source and the radiation detector around the subject, emits radiation at various angles to capture a plurality of radiological images, reconstructs a tomographic image, using the radiological images captured at each angle, and displays an arbitrary tomographic image.

In the above-described embodiment, the radiography apparatus to which the radiological image display device according to the invention is applied is used as an apparatus which captures the radiological image of the breast. However, the subject is not limited to the breast. For example, a radiography apparatus which captures the image of the chest or the head may be used.

Next, the operation and effect of other embodiments of the invention will be described.

A pseudo two-dimensional image is generated from a plurality of tomographic images and a temporary depth map in which each position on the pseudo two-dimensional image is associated with depth information indicating the position of the tomographic plane corresponding to each position in the depth direction is created. Then, a depth map is created on the basis of the temporary depth map and the corresponding positional relationship between each position on the two-dimensional radiological image and each position on the pseudo two-dimensional image. According to this structure, even when the two-dimensional radiological image and the tomographic image have different geometric shapes due to a difference in the imaging time, it is possible to reliability associate each position on the two-dimensional radiological image with the tomographic plane.

In some cases, when tomosynthesis imaging is performed, a pseudo two-dimensional image is generated from the tomographic image acquired by tomosynthesis imaging and is used as a two-dimensional radiological image for display, in order to reduce the exposure dose of the subject. However, when the tomographic image is reconstructed from a plurality of radiological images captured by tomosynthesis imaging, a filter process suitable for displaying the tomographic image is performed. Therefore, in some cases, the pseudo two-dimensional image generated from the reconstructed tomographic image is not suitable for display. For this reason, the pseudo two-dimensional image is generated as the two-dimensional radiological image from a tomographic image different from the plurality of tomographic images. Therefore, the pseudo two-dimensional image can be suitable for display.

In addition, a depth map in which each position on the two-dimensional radiological image and depth information indicating the position of the tomographic plane corresponding to each position in the depth direction are associated with each other is created on the basis of the correlation between each position on the two-dimensional radiological image and a plurality of tomographic images. Therefore, it is possible to easily associate each position on the two-dimensional radiological image with the position of the tomographic plane in the depth direction.

What is claimed is:

1. An image display device comprising:
   a display unit for displaying at least one of a two-dimensional radiological image and a plurality of tomographic images of the same subject;
   a depth map creation unit for creating a depth map in which each position on the two-dimensional radiological image is associated with depth information indicating a position of a tomographic plane corresponding to each position in a depth direction; and
   a pseudo two-dimensional image generation unit for generating a pseudo two-dimensional image from the plurality of tomographic images,
   wherein the depth map creation unit creates a temporary depth map in which each position on the pseudo two-dimensional image is associated with depth information indicating a position of a tomographic plane corresponding to each position in the depth direction and creates the depth map, based on the temporary depth map and a correspondence relationship between each position on the two-dimensional radiological image and each position on the pseudo two-dimensional image.

2. The image display device according to claim 1, wherein the depth map creation unit creates the depth map on the basis of a positional relationship between a position of a radiation source when the two-dimensional radiological image is captured and a position of a detection unit for acquiring the two-dimensional radiological image.

3. The image display device according to claim 1, wherein the depth map creation unit deforms the temporary depth map, on the basis of the correspondence relationship between each position on the two-dimensional radiological image and each position on the pseudo two-dimensional image, to create the depth map.

4. The image display device according to claim 1, further comprising:
   a pseudo two-dimensional image generation unit for generating a pseudo two-dimensional image from the plurality of tomographic images,
   wherein the depth map creation unit associates each position on the pseudo two-dimensional image with depth information indicating a position of a tomographic plane corresponding to each position in the depth direction, to create the depth map.

5. The image display device according to claim 1, further comprising:
   a two-dimensional image generation unit for generating a pseudo two-dimensional image as the two-dimensional radiological image from a tomographic image which is different from the plurality of tomographic images and is acquired by a reconstruction process,
   wherein the depth map creation unit creates a depth map in which each position on the generated two-dimensional radiological image is associated with the depth information indicating a position of a tomographic plane corresponding to each position in the depth direction.

6. The image display device according to claim 1, wherein the depth map creation unit associates each position on the two-dimensional radiological image with the depth information indicating the position of the tomographic plane corresponding to each position in the depth direction, on the basis of a correlation between each position on the two-dimensional radiological image and the plurality of tomographic images, to create the depth map.

7. The image display device according to claim 1, wherein the depth map creation unit divides the two-dimensional radiological image into a plurality of areas and associates a position of each area on the two-dimensional radiological image with depth information indicating a position of a tomographic plane corresponding to the position of each area in the depth direction, to create the depth map.

8. The image display device according to claim 1, further comprising:
   a display control unit for specifying depth information of a predetermined position on the two-dimensional radiological image, with reference to the depth map, and displaying a tomographic image of a tomographic plane indicated by the specified depth information on the display unit.

9. The image display device according to claim 8, further comprising:
   an input unit for receiving an arbitrary position which is designated on the two-dimensional radiological image displayed on the display unit,
   wherein the display control unit displays the tomographic image on the display unit, using the designated position as the predetermined position.

10. The image display device according to claim 8, further comprising:
    an abnormal shadow detection unit for detecting an abnormal shadow included in the two-dimensional radiological image,
    wherein the display control unit displays the tomographic image on the display unit, using a position of the detected abnormal shadow as the predetermined position.

11. The image display device according to claim 1, wherein the display unit displays the tomographic image and the two-dimensional radiological image side-by-side.

12. The image display device according to claim 1, wherein the display unit displays the tomographic image so as to be superimposed on the two-dimensional radiological image.

13. A radiological image capture and display system comprising:
    an imaging unit for acquiring a two-dimensional radiological image and a plurality of tomographic images of the same subject; and
    the image display device according to claim 1.

14. An image display method comprising:
- displaying at least one of a two-dimensional radiological image and a plurality of tomographic images of the same subject;
- creating a depth map in which each position on the two-dimensional radiological image is associated with depth information indicating a position of a tomographic plane corresponding to each position in a depth direction; and
- generating a pseudo two-dimensional image from the plurality of tomographic images,
- wherein the creating comprises creating a temporary depth map in which each position on the pseudo two-dimensional image is associated with depth information indicating a position of a tomographic plane corresponding to each position in the depth direction and creating the depth map, based on the temporary depth map and a correspondence relationship between each position on the two-dimensional radiological image and each position on the pseudo two-dimensional image.

15. A non-transitory recording medium having stored therein a program that causes a computer to perform an image display method comprising:
- displaying at least one of a two-dimensional radiological image and a plurality of tomographic images of the same subject;
- creating a depth map in which each position on the two-dimensional radiological image is associated with depth information indicating a position of a tomographic plane corresponding to each position in a depth direction; and
- generating a pseudo two-dimensional image from the plurality of tomographic images,
- wherein the creating of the depth map comprises creating a temporary depth map in which each position on the pseudo two-dimensional image is associated with depth information indicating a position of a tomographic plane corresponding to each position in the depth direction and creating the depth map, based on the temporary depth map and a correspondence relationship between each position on the two-dimensional radiological image and each position on the pseudo two-dimensional image.

16. An image display device comprising:
- a pseudo two-dimensional image generation unit for generating a pseudo two-dimensional image from a plurality of tomographic images of the same subject;
- a display unit for displaying at least one of the pseudo two-dimensional image and the plurality of tomographic images; and
- a depth map creation unit for creating a depth map in which each position on the pseudo two-dimensional image is associated with depth information indicating a position of a tomographic plane corresponding to each position in a depth direction,
- wherein the display unit further displays a scale indicating the position of the tomographic plane in the depth direction, said scale displayed in a same display area with the displayed image.

17. An image display method comprising:
- generating a pseudo two-dimensional image from a plurality of tomographic images of the same subject;
- displaying at least one of the pseudo two-dimensional image and the plurality of tomographic images; and
- creating a depth map in which each position on the pseudo two-dimensional image is associated with depth information indicating a position of a tomographic plane corresponding to each position in a depth direction; and
- displaying a scale indicating the position of the tomographic plane in the depth direction, said scale displayed in a same display area with the displayed image.

18. A non-transitory recording medium having stored therein a program that causes a computer to perform an image display method comprising:
- generating a pseudo two-dimensional image from a plurality of tomographic images of the same subject,
- displaying at least one of the pseudo two-dimensional image and the plurality of tomographic images;
- creating a depth map in which each position on the pseudo two-dimensional image is associated with depth information indicating a position of a tomographic plane corresponding to each position in a depth direction; and
- displaying a scale indicating the position of the tomographic plane in the depth direction, said scale displayed in a same display area with the displayed image.

* * * * *